US007769213B2

(12) United States Patent
Gregory et al.

(10) Patent No.: US 7,769,213 B2
(45) Date of Patent: Aug. 3, 2010

(54) APPARATUS FOR PREDICTING BONE FRACTURE RISK

(75) Inventors: Jennifer Susan Gregory, Aberdeen (GB); Richard Malcolm Aspden, Aberdeenshire (GB); David Macaulay Reid, Aberdeen (GB)

(73) Assignee: Aberdeen University Research and Innovation (GB)

( * ) Notice: Subject to any disclaimer, the term of this patent is extended or adjusted under 35 U.S.C. 154(b) by 388 days.

(21) Appl. No.: 10/577,359

(22) PCT Filed: Nov. 1, 2004

(86) PCT No.: PCT/GB2004/004603

§ 371 (c)(1),
(2), (4) Date: Feb. 21, 2007

(87) PCT Pub. No.: WO2005/045730

PCT Pub. Date: May 19, 2005

(65) Prior Publication Data

US 2007/0274442 A1    Nov. 29, 2007

(30) Foreign Application Priority Data

Oct. 31, 2003    (GB)    ................... 0325523.9

(51) Int. Cl.
*G06K 9/00*    (2006.01)
*G01B 15/02*    (2006.01)

(52) U.S. Cl. ...................... 382/128; 382/132; 382/130; 382/131; 382/104; 378/54; 378/169; 378/50; 600/407

(58) Field of Classification Search ................... 378/51, 378/54, 56, 197, 22, 169, 50; 600/425; 382/128, 382/130, 131, 132, 156, 168, 283, 104
See application file for complete search history.

(56) References Cited

U.S. PATENT DOCUMENTS 5,931,780 A * 8/1999 Giger et al. ................. 600/407

(Continued)

FOREIGN PATENT DOCUMENTS

WO    WO 94/06351    3/1994

OTHER PUBLICATIONS

Gregory et al ( Hip fractures, morphometry and geometry, Apr. 2002).*

(Continued)

*Primary Examiner*—Wesley Tucker
*Assistant Examiner*—Nancy Bitar
(74) *Attorney, Agent, or Firm*—Studebaker & Brackett PC; Donald R. Studebaker (57) ABSTRACT

An apparatus is disclosed for predicting bone fracture risk in an osteoporotic patient. The apparatus comprises a Dual X-ray Absorptiometry scanner for scanning a body area of the patient and producing a Dual X-ray Absorptiometry image of the body area, and image analysis means for analyzing predetermined aspects of the Dual X-ray Absorptiometry image. The apparatus further comprises data comparison means comprising a database of comparative data sets from Dual X-ray Absorptiometry images of control subjects to predict the risk of bone fracture in the patient. The image analysis means preferably analyses the shape of a body past using an Achieve Shape Model or analyses the texture of a body past using Fourier Transforms and Principal Component Analysis.

34 Claims, 6 Drawing Sheets

U.S. PATENT DOCUMENTS

| | | | | |
|---|---|---|---|---|
| 6,038,281 | A * | 3/2000 | Mazess | 378/54 |
| 6,205,348 | B1 * | 3/2001 | Giger et al. | 600/407 |
| 7,379,529 | B2 * | 5/2008 | Lang | 378/54 |
| 7,660,453 | B2 * | 2/2010 | Lang | 382/132 |
| 2005/0010106 | A1 * | 1/2005 | Lang et al. | 600/425 |

OTHER PUBLICATIONS

Prediction of Hip Fracture Can Be Significantly Improved by a Single Biomedical Indicator, 2002.*

J.S. Gregory et al., "Hip Fractures, Morphometry and Geometry", Department of Orthopedics, University of Aberdeen, United Kingdom, XP-002318247.

J.S. Gregory et al., "A method for assessment of the shape of the proximal femur and its relationship to osteoporotic hip fracture", International Osteoporosis Foundation and National Osteoporosis Foundation, Nov. 7, 2003, pp. 5-11, United Kingdom, XP-002318248.

C. Bergot et al., "Hip Fracture Risk and Proximal Femur Geometry from DXA Scans", International Osteoporosis Foundation and National Osteoporosis Foundation, 2002, pp. 542-550, United Kingdom, XP-002318249.

C.J. Taylor, "Model-based interpretation of complex and variable images", Department of Medical Biophysics, 1997, United Kingdom, XP-002318250.

J.S. Gregory et al., "Analysis of Trabecular Bone Structure Using Fourier Transforms and Neural Networks", IEEE Transactions on Information Technology in Biomedicine, vol. 3, No. 4, Dec. 1999, pp. 289-294, XP-002318251.

Sharmila Majumdar et al., "Fractal analysis of radiographs: Assessment of trabecular bone structure and prediction of elastic modulus and strength", Magnetic Resonance Science Center and Osteoporosis and Arthritis Research Group, Department of Radiology, University of California, San Francisco, California 94143, Med. Phys. 26 (7), Jul. 1999.

Slison Stewart et al., "Done Density and Bone Turnover in Patients with Osteoarthritis and Osteoporosis", The Journal of Rheumatology 1999; 26:3 pp. 622-626.

Communication pursuant to Article 94(3) EPC; Examination Report dated Dec. 15, 2009; Application No. 04 798 339.0-1526.

* cited by examiner

APPARATUS FOR PREDICTING BONE FRACTURE RISK

The present invention relates to apparatus for predicting bone fracture risk, in particular for predicting bone fracture risk in an osteoporotic patient.

Osteoporosis (OP) is a disease of the bones in which a reduction in bone density causes bone weakness. A patient is defined as suffering from OP by the World Health Organisation if their bone mineral density (BMD) is less than 2.5 standard deviations below the young mean value, BMD being a measure of the quantity of bone in a given volume or area. In OP, bone material is gradually lost, until the bone becomes so weak as to be susceptible to fracture at relatively low impacts.

The current best method for measuring BMD is believed to be Dual X-ray Absorptiometry (DXA). DXA is used both for the diagnosis of OP and for assessment of treatment efficacy. DXA systems employ two X-ray beams of different energies. BMD is calculated from the absorption of each X-ray beam by bone, after subtracting absorption by soft tissue. A digital image can be produced on a display attached to the DXA scanner, the pixel value at any point representing the BMD value.

Patients are often unaware that they are suffering from OP, since there are few or no warning signs until a fracture actually occurs, unless a bone scan has been performed. OP treatment is generally assessed either in terms of fracture prevention, or by increases in BMD, as an indicator of fracture prevention.

A common fracture site in OP patients is the hip, i.e. the proximal femur. The shape of the proximal femur is known to be an important factor in predicting fracture in OP patients. Images of the proximal femur for shape analysis are typically obtained from radiographs, i.e. "normal" X-rays.

Traditionally, proximal femur shape has been measured geometrically, for example by measuring the femoral neck length, the neck shaft angle, or the cross sectional moment of inertia. Alternatively, proximal femur shape can be assessed using finite element models, i.e. computer software-generated engineering models which divide an image of the femur into "elements", and calculate the forces in each element generated by applying a given force at a particular point.

However, both geometric and finite element analyses of femur shape have limitations. Thus, geometric measurements are easy to obtain and analyse, but only provide an analysis of individual components in a complex structure: the strength of the femur, and hence the risk of fracture, is affected by all of the structural features, and their interaction with each other. Furthermore, it is difficult to extrapolate the effects of changes in individual measurements, since each individual measurement is not only correlated with every other measurement, but also with factors such as the height and weight of the patient. In contrast, finite element analysis is computationally expensive, with a separate model being created and tested for each patient.

Attempts have also been made to measure bone strength, by "texture" analysis, i.e. by quantifying bone structure rather than bone shape. Such analyses have been performed on radiograph images, for example, from visual scoring systems, such as the Singh index, to more sophisticated computerised techniques based on fractal analysis and other image processing methods. Recently, fractal analysis has been the predominant method of texture analysis, although it has not categorically been established as preferable to other methods of texture analysis.

The present invention seeks to provide apparatus for predicting fracture risk in OP patients which overcomes the aforementioned limitations of known approaches to fracture risk analysis.

According to the present invention there is provided apparatus for predicting bone fracture risk in an osteoporotic patient, which apparatus comprises a Dual X-ray Absorptiometry scanner for scanning a body part of the patient and producing a Dual X-ray Absorptiometry image of the body area; image analysis means for analysing pre-determined aspects of the Dual X-ray Absorptiometry image, the aspects being pre-determined according to the body part being scanned, and for generating an image data set from the Dual X-ray Absorptiometry image; and data comparison means comprising a database of comparative data sets from Dual X-ray Absorptiometry images of control subjects, for comparison with the image data set for the Dual X-ray Absorptiometry image of the patient, to thereby predict the risk of bone fracture in the patient.

The present invention thus provides apparatus which can be used to simply and easily predict the risk of bone fracture in a patient without the need for expert analysis of the DXA image. By pre-determining the aspects of the DXA image which are to be analysed, and by having a database of comparison data sets from control subjects for those aspects already stored in the apparatus, the apparatus of the present invention can automatically provide a prediction of fracture risk in the patient. The control subjects preferably comprise both fracture and non-fracture subjects.

The apparatus of the present invention comprises a Dual X-ray Absorptiometry (DXA) scanner for scanning a body part of a patient and producing a DXA image of that body part. Any suitable DXA scanner may be used, as are commercially available and known in the art.

The apparatus of the present invention also comprises image analysis means for analysing pre-determined aspects of the DXA image. The aspects of the image to be analysed are pre-determined according to the part of the body being scanned. Thus, the aspects of an image of a proximal femur for analysis will be different from those of a wrist, ankle, hand, spine, and so forth. Thus, if the apparatus is to be used for predicting fracture risk in the proximal femur of a patient, then the particular pre-determined aspects of a proximal femur image are those which will be analysed by the image analysis means.

The image analysis means preferably analyses the DXA image by analysis of the shape of the particular body part or by analysis of the texture of the body part.

A preferred method of shape analysis is by use of an Active Shape Model. An Active Shape Model (ASM) is an image processing model which can be used to analyse shapes which have common features, but which are subject to natural variation, such as a human body part. An ASM is a mathematical model which can be used to quantify differences in the shape of a body part, for example the proximal femur, between an OP patient, and a control subject.

As discussed above, the image analysis means used in the present invention analyses pre-determined aspects of the DXA image. In those preferred embodiments in which the image analysis means uses an ASM, a model is built to measure those particular aspects of the image, and is stored in the apparatus. The particular model which is built will thus be different for each different body part being analysed, since each different body part has different significant aspects for analysis.

Thus, using an ASM, a number of landmark points (i.e. aspects) of the DXA image are selected for analysis to determine the outline of a particular body part, i.e. a model is built. Thus, for a proximal femur the landmark points may include, for example, the tip of the greater trochanter, and the narrowest point of the femoral neck. The coordinates of these points are measured and used to calculate the morphometry of the body part, i.e. a data set for that ASM is generated.

In a given particular model, a number of independent shape variation components may be produced by the ASM, some or all of which may be associated with fracture. For example, where a proximal femur shape is being analysed, each of the components may describe a characteristic of the shape of the femur, and may combine features such as the hip axis length and neck-shaft angle. For a particular model, discriminant analysis is preferably applied to determine which variable or combination of variables is best able to predict fracture risk. An ASM has an advantage over conventional geometrical analysis of bone shape in that the whole outline of the bone is measured, through pre-determined landmark points, rather than individual geometrical properties.

The ASM data set generated from the DXA image of the patient may be compared with the comparative data sets in the database, for example by examining how the location of the landmark points deviates from the mean co-ordinates of the comparative data sets, from which fracture risk may be predicted.

A preferred toolkit for producing ASMs for use in the apparatus of the present invention is the ASMTk from Visual Automation Limited, Manchester, UK, which runs within the MATLAB software environment (The MathWorks Inc., Natick, USA).

An alternative preferred means of analysis by which the image analysis means used in the present invention may analyse the DXA image is by analysis of the texture of the body part.

A preferred method of texture analysis uses Fourier transforms and Principal Component Analysis to generate a mathematical model of the DXA image data.

Principal Component Analysis (PCA) is a data reduction technique which describes data in terms of orthogonal, linearly independent components. A relatively small number of components, comprising linear combinations of the original variables, thus contain the majority of the information. PCA has no preconditions, such as relying on the data to fit a normal or fractal distribution, but builds a mathematical model based on the correlations present in the data, which can then be used to investigate the similarities and differences between bone structure, for example trabecular bone structure, in a patient and a control group.

In preferred embodiments of the present invention which use texture analysis to analyse the DXA image, the DXA image is preferably digitised and regions of interest identified in the image. For example, where a proximal femur is being analysed, the regions of interest may, for example, be located at the femoral head and neck. A power spectrum may be obtained from a Fourier transform of each region of interest, and profiles of each region produced. PCA may then be used to generate a data set from each profile, which can be compared with the database of comparative data sets.

The image analysis means used in the apparatus of the present invention may use one or more image analysis methods. Thus, the image analysis means may use both shape and texture analysis, as described above. For example, the image analysis means may analyse the DXA image using both an ASM and Fourier transforms and Principal Component Analysis.

The apparatus of the present invention comprises data comparison means comprising a database of comparative data sets from Dual X-ray Absorptiometry images of control subjects, for comparison with the image data set for the Dual X-ray Absorptiometry image of the patient, to thereby predict the risk of bone fracture in the patient. Thus, a series of DXA images of control subjects are taken, for example in the case of fracture risk prediction in OP patients the control subjects would be persons not suffering from OP, and analysed by the image analysis means to generate a data set for the DXA image of each control subject. For example, if the image analysis means uses an ASM, then the same ASM is used to analyse each of the DXA images of the control subjects. If the image analysis means uses both an ASM and Fourier transforms and Principal Component Analysis, then both of these methods of image analysis are performed on each of the DXA images of the control subjects. In this way, a database of comparative data sets from the control subjects is created, and stored in the apparatus, appropriate to the method of image analysis being used to analyse the DXA image of the patient.

The apparatus of the present invention may be used for predicting fracture risk in different body parts, for example the proximal femur, wrist, ankle, hand or spine. Each different body part will have significant aspects for analysis, for example landmark points when using shape analysis, or regions of interest when using texture analysis, and these aspects are predetermined and stored in the apparatus. In addition, a database of comparative data sets from control subjects for those aspects for each body part is also stored in the apparatus. In use, the operator thus initially merely selects which body part is to be analysed, and the apparatus accordingly selects the appropriate aspects of the DXA image for analysis, and the appropriate database of comparative data sets for comparison therewith.

The apparatus of the present invention uses DXA image analysis to predict fracture risk. As discussed above, DXA images are conventionally used for determining BMD. Accordingly, the fracture risk prediction value determined by the image data set comparison may used in combination with the standard BMD data obtained from the DXA image, to provide a more accurate prediction of fracture risk. Thus, the apparatus of the present invention may be used to accurately predict fracture risk by comparing the results of ASM and Fourier transforms and Principal Component Analysis of the DXA image, together with the standard BMD data obtained directly from the DXA image.

Although the apparatus of the present invention is principally directed to predicting fracture risk in OP patients, it is not limited in application thereto, and may also be applied for use with patients with other disorders which affect the shape or trabecular structure of bone. For example, the apparatus of the present invention may be used to measure the progress of osteoarthritis or Paget's disease, by quantifying the deformation of the femur. The apparatus may also be used for measuring non-pathological changes in a subject associated with age, gender, body mass index and/or genetics.

Embodiments of the present invention will now be described in detail with reference to the accompanying drawings in which.

EXAMPLE 1

A) Materials and Methods

I) Image Acquisition

Data were taken from a previous study [Stewart, A., Black, A., Robins, S. P., and Reid, D. M. Bone Density and Bone Turnover in Patients with Osteoarthritis and Osteoporosis. J Rheumatol 1999 263:622-626]. Although this study had included subjects with osteoarthritis, they were excluded, leaving 30 patients who had sustained a hip fracture at least 3 years prior to DXA examination and 30 control subjects matched for age. All patients had undergone a scan of their unfractured hip and a total body scan by DXA using a Norland XR-26 scanner. The controls had had their left hip scanned. Five BMD and Bone Mineral Content (BMC) values were used: total body BMD, total body BMC, femoral neck BMD (NECK BMD), trochanteric BMD (TROCH BMD) and Ward's triangle BMD (WARDS BMD). A pelvic anteroposterior radiograph, which had been recorded within a year of the DXA scan, was also used. All subjects were ambulant out-patients at the time of study and did not have increased bone turnover as assessed by pyridinoline/creatinine and deoxypyridinolone/creatinine ratios, so that immobility induced or post-fracture osteopenia is unlikely.

The Radiographs were digitised using a Howtek Multi-RAD 850 scanner (Howtek, Hudson, N.H.) at a resolution of 73 dpi (348 mm per pixel) and a depth of 8 bits. The quality of the digitised radiographs was assessed and the image was discarded if the outline of the femur below the greater trochanter was not wholly visible on the radiograph, or if the image the outline could not properly be identified. This left a dataset of 50 images; 26 hip fracture patients (HIP) and 24 controls (CNT).

II) Active Shape Model (ASM) Design

An ASM of the proximal femur was created using an active shape modelling toolkit (ASMTk) (Visual Automation Limited, Manchester, UK), a software program which runs within the MATLAB (The MathWorks Inc, Natick, USA) software environment. A representative subset of the images was chosen as a training set. A series of landmark points which identify key features of the femur, including the tip of the greater trochanter and the narrowest point of the femoral neck, were marked on each image. The same number of landmark points was used for each image in the model and each point always refers to the same feature in the shape. The software first aligned the shapes by scaling, rotating and translating them in order to minimise the variance, in distance, between equivalent points. This process means that all data about the shape is stored proportionally, rather than absolutely, and the effects of the overall size of the femur on measurements such as neck length, neck width and shaft width are eliminated. The size of the femur was recorded as the ratio between the area of the outline and the average area of all the outlines and saved as a separate variable, Fscale.

Figure 1A:
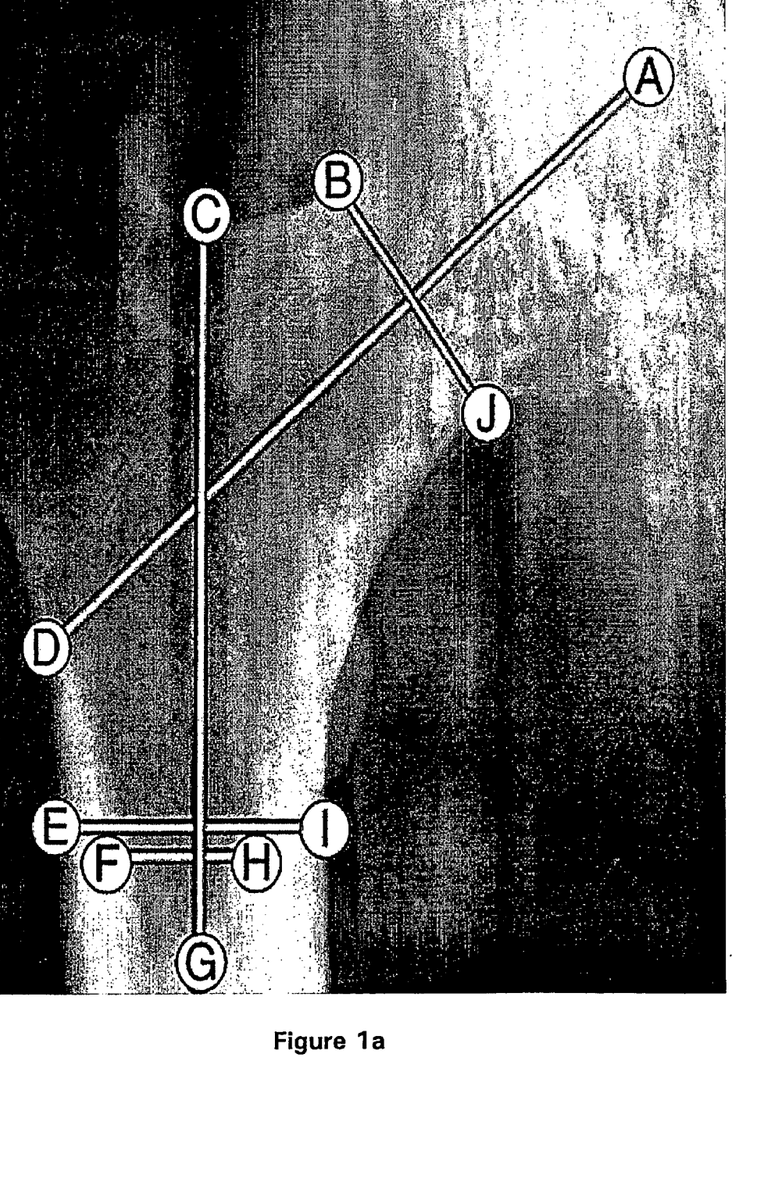
FIG. 1 shows a typical radiograph of the proximal femur showing the positions of landmark points for different Active Shape Models to be used to analyse the shape of the femur: (a) Model 1, 10 points (b) Model 2, 10 points (c) Model 3, 20 points (d) Model 4, 29 points)
Figure 1B:
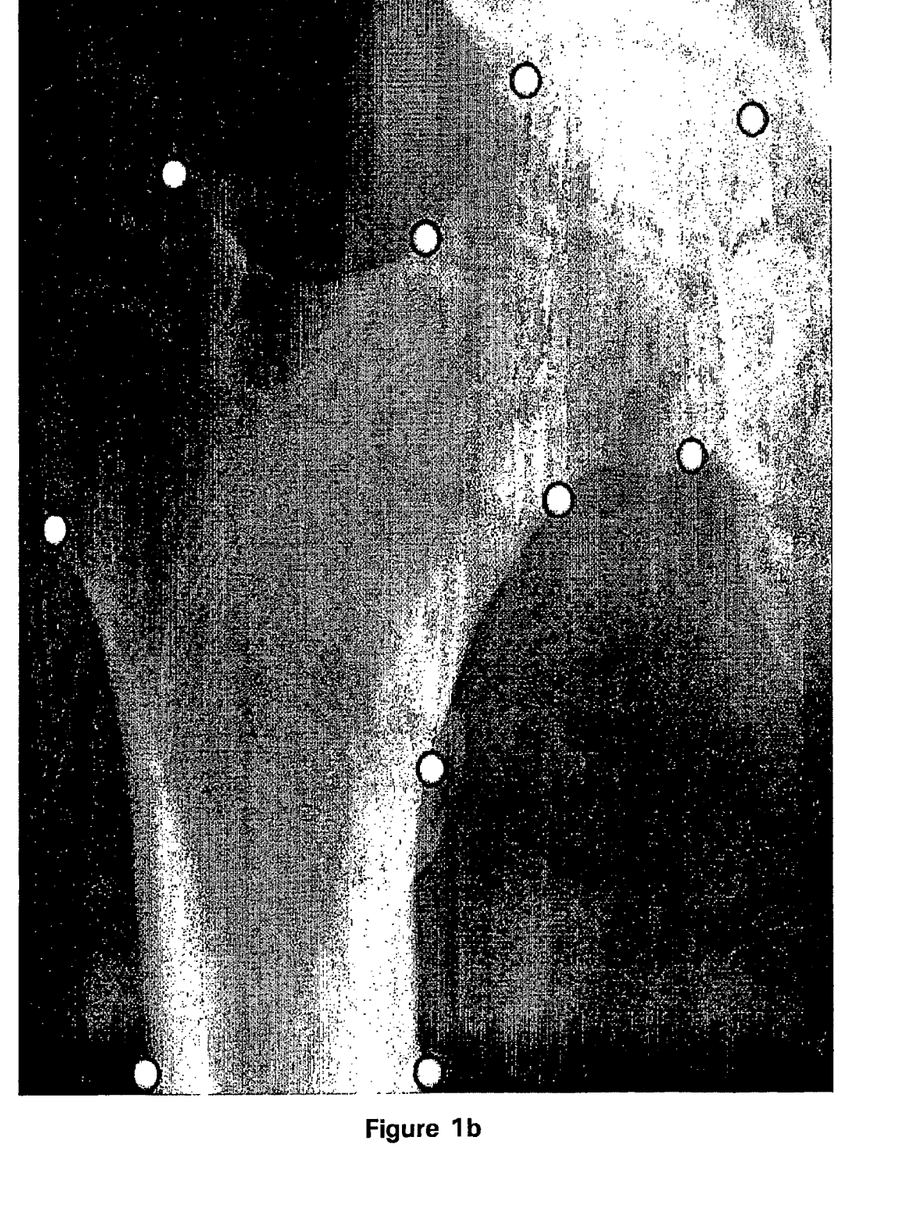
Figure 1C:
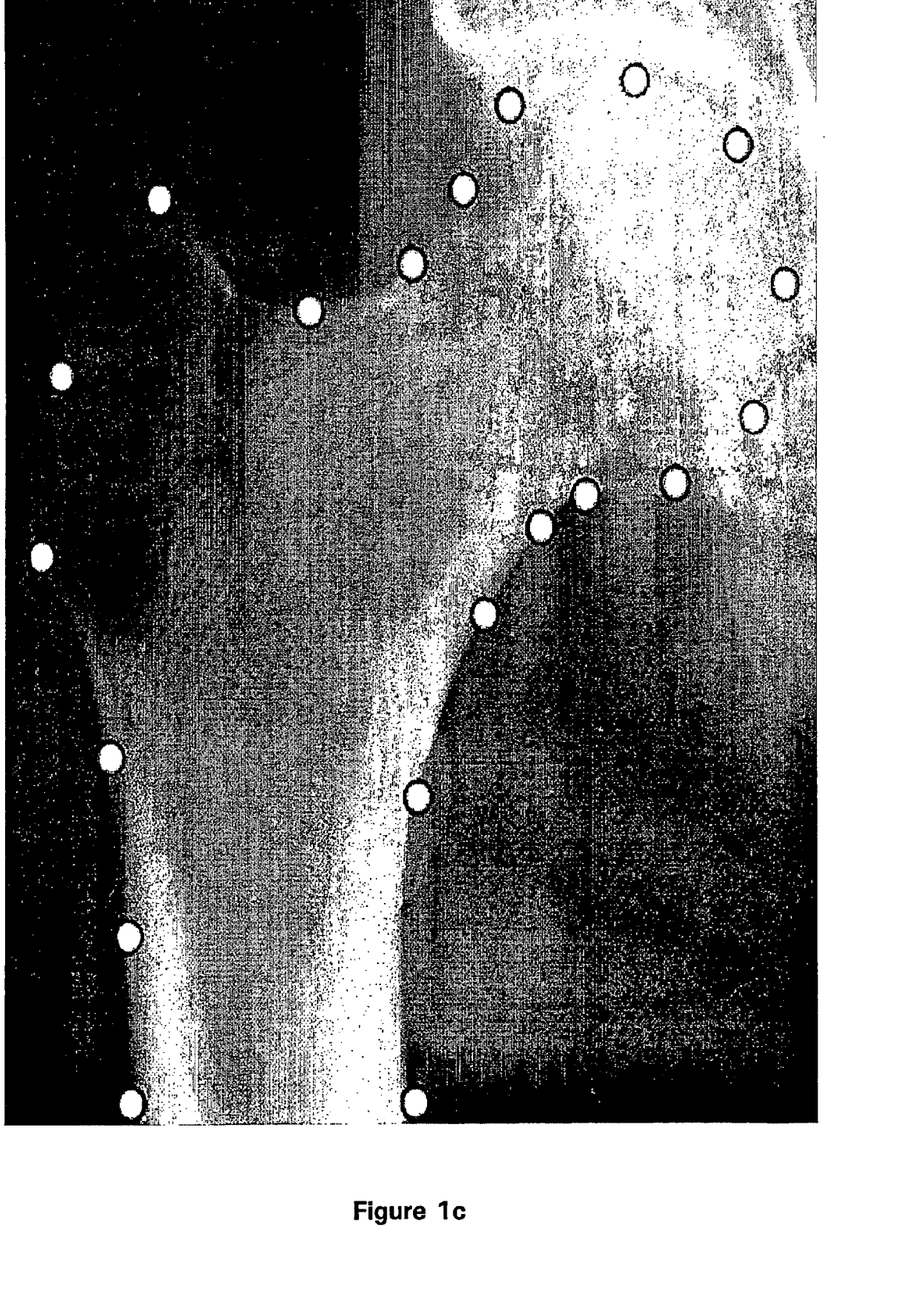
Figure 1D:
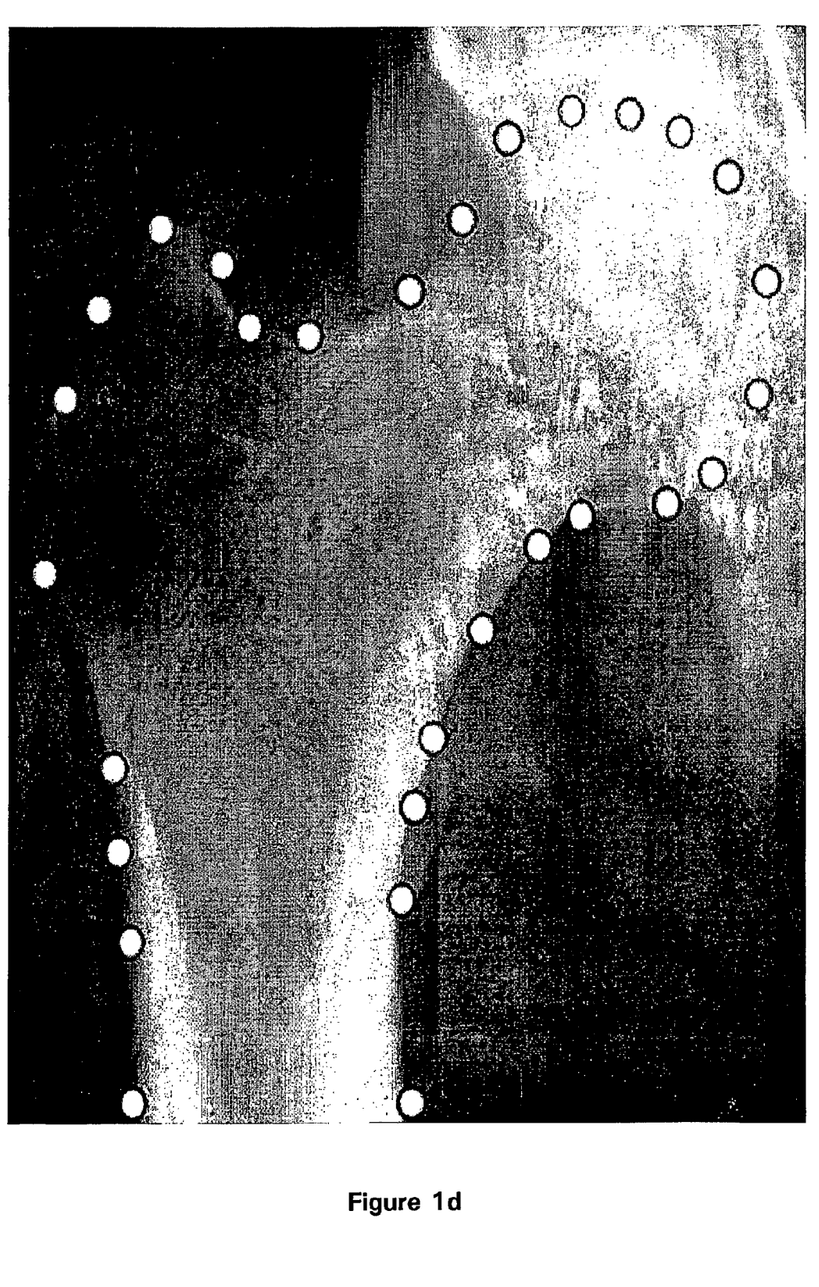

Twenty images were randomly selected to create a training set. Five different models were created, using different numbers of landmark points, and tested for relative accuracy and repeatability. The landmark points were marked manually for each model on each image. Model 1 (FIG. 1a) comprised 10 landmark points which mark the main femoral axes, as are used in studies of femoral geometry. These corresponded to the neck axis length (distance A-D), the neck width (distance B-J), the shaft width (distance E-I) and the intramedullary diameter (distance F-G). Model 2 (FIG. 1b) comprised 10 landmark points which describe the main features of the outline including the shaft, femoral head, neck and greater trochanter, but excluding the lesser trochanter, because of its variable appearance related to hip positioning. Models 3 and 4 were more detailed versions of Model 2, comprising 20 and 29 landmark points respectively (FIGS. 1c, 1d). Because the length of shaft visible in the radiographs varied greatly across the subject group, and a number of radiographs showed no part of the shaft below the lesser trochanter, a further model, Model 5 (FIG. 2), was designed. Model 5 comprised 29 points describing the outline of the femur, including the outline of the lesser trochanter, to compare with its omission from the other models, but excluding the shaft below that region.

To compare the models after training, two measures of repeatability were calculated on the training set for each of the models using the ASMTk. Each of the 20 training images was loaded in turn, and the trained model automatically searched for the outline of the femur, starting from the mean shape and pose. The shape identified automatically by. the ASMTk was then compared with the manually labelled shape prepared for the training set using two error estimators. The point-to-point error was calculated as the mean distance, in pixels, between the original, manually generated, points and those automatically generated by the software. The point-to-line error was the mean distance between the automatically generated landmark points and lines tangential to the outline at each of the corresponding points on the manually labelled images.

The best model was thus chosen, and the remaining images were analysed using this model. The independent modes of variation were found for each image using Principal Component Analysis and used as inputs to the statistical analysis. Each mode of variation is a linear combination of the original variables (viz. the x and y co-ordinates of each landmark point) and is selected so as to be orthogonal, and therefore linearly independent, of all the other modes. When combined, the modes of variation account for 100% of the variance in the original data set. Each mode is ordered according to the amount of variation explained: lower numbered modes account for the largest percentage of variance, whilst higher numbered modes, in this case, greater than mode 10, explain little variance and can be treated as noise.

III) Geometrical Analysis

Figure 2:
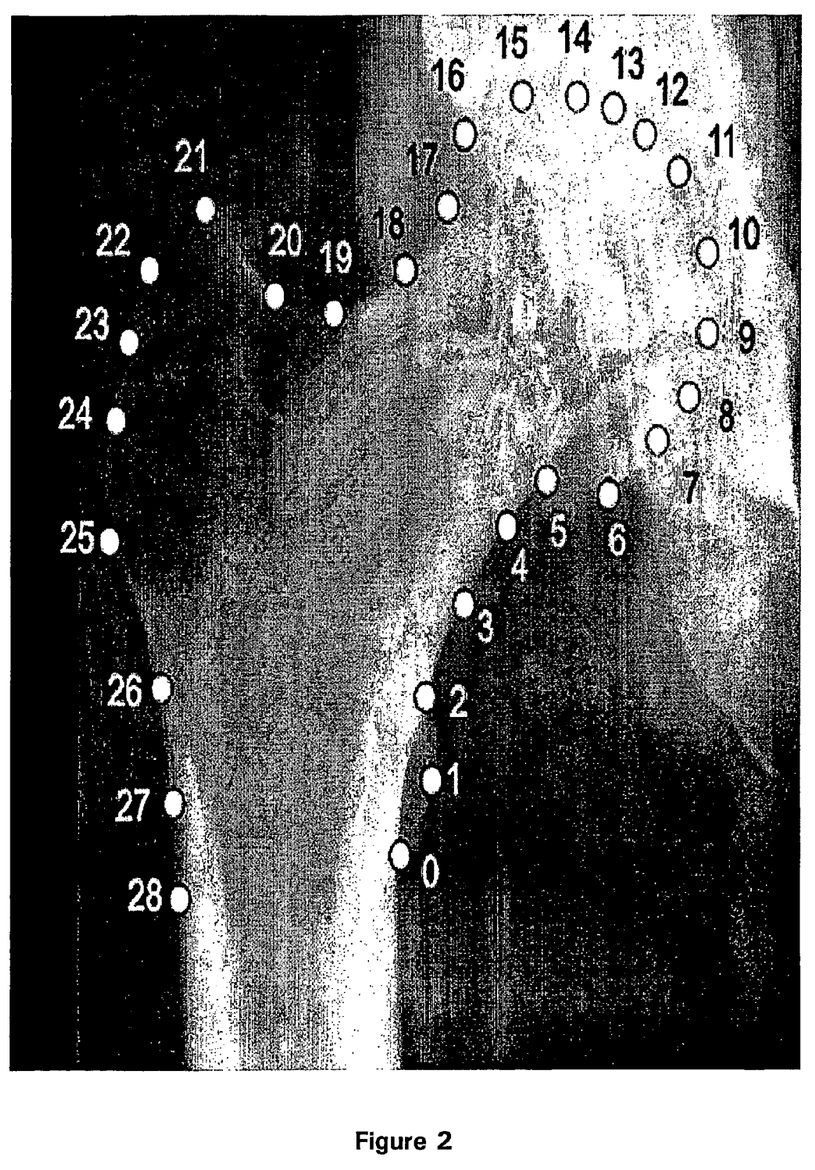
FIG. 2 shows landmark points on a typical radiograph of the proximal femur for Active Shape Model 5, from which geometrical measurements were also obtained by calculating the distance between numbered landmark points, viz. Neck Length (N-Len) between points 11 and 26, Neck Width (N-Wid) between points 4 and 18, and Head Diameter (H-Diam) between points 16 and 8.

Three conventional geometrical measurements were calculated from the radiographs for comparison: neck axis length (N-Len), femoral neck width (N-Wid) and femoral Head Diameter (H-Diam). These measurements were calculated using the co-ordinates of the landmark points of the ASM (FIG. 2).

The geometrical properties of the femur are known to be highly correlated with each other and with the height and weight of an individual, but by using ratios of two measurements instead of single measurements the influence of these effects can be reduced. Thus, compound variables were created, N-Wid/N-Len and H-Diam/N-Len. A number of radiographs used in the study showed little or nothing of the shaft below the lesser trochanter, and so the model used did not analyse the femur below this point. For this reason, neither the width of the shaft or the neck-shaft angle were measured reliably, and these measurements were excluded from the study.

IV) Statistical Analysis

All variables were tested for significant differences between the two groups using Student's t-test, if the variable passed a normality test, or a Mann-Whitney Rank Sum test otherwise (SigmaStat 2.0, SPSS Science, Chicago). Stepwise linear discriminant analysis was used to estimate the probability that a given subject would belong to the fracture group. If this probability was greater than 0.5, the subject was assigned to the fracture group. As the modes are generated using Principal Components Analysis, each mode is linearly independent of all other modes, so problems associated with stepwise methods due to multicollinearity are avoided. The probability generated by this process was saved as a new variable, Pshape, for use in combination with BMD values. The same method was also used to create a classifier from the geometrical measurements.

Linear discriminant analysis was used to assess both the strength of single variables and combinations of variables. Discriminant analysis was used in conjunction with binary logistic regression to calculate the odds ratio associated with each variable. SPSS v10 statistical software (SPSS Science, Chicago) was used for both discriminant and logistic analysis.

B) Results

I) Model Testing

Using the point-to-point and point-to-line errors as estimators of the accuracy of each model, Model 5 was the most accurate (Table 1).

TABLE 1

| Model | Number of landmark points | Median Point-to-Point Error (mm) | Median Point-to-Line Error (mm) |
|---|---|---|---|
| 1 | 10 | 8.5 | 6.6 |
| 2 | 10 | 5.8 | 4.2 |
| 3 | 20 | 3.3 | 2.0 |
| 4 | 29 | 3.3 | 2.0 |
| 5 | 29 | 2.2 | 1.3 |

Model 5 located the outline of the femur with a median point-to-point error of 6.22 pixels (2.17 mm) and a median point-to-line error of 3.81 pixels (1.32 mm) when comparing the automatically located points with those inputted manually on the training set. This model was used in the subsequent analysis. The search is reset to start from the same outline each time (the mean shape and position of the outlines stored in the model) and is thus fully automated, being repeatable, finding exactly the same points, each time an image is analysed.

II) Statistical Analysis

There were no significant differences in the age, height, weight or body mass index between the fracture and control groups.

All the modes of variation found by the ASMTk were normally distributed and two of the modes (numbers 2 and 7) were significantly different between the two groups ($P<0.05$, t-test). The size of the femur (Fscale) was not significantly different between the HIP and CNT subjects ($P=0.34$). Four of the five BMD measurements showed statistically significant differences between the two groups ($P<0.01$), the exception being Total Body BMD ($P=0.11$). None of the geometrical measurements or ratios showed statistically significant differences between the two groups. The values found are summarised in Table 3.

Table 3 shows the mean values of all the variables measured from 26 fracture patients (HIP) and 24 controls (CNT) and the significance of the difference between these two groups. The results indicate that the data were not normally distributed (Kolmogorov-Smirnov test), and the. Mann-Whitney test was used instead of the t-test and the 25% and 75% confidence limits shown instead of the standard deviation. Variables showing significant differences between the groups are in bold.

TABLE 3

| Variable | HIP | | CNT | | P-value |
|---|---|---|---|---|---|
| | Mean | SD | Mean | SD | |
| Bone Mineral Density Measurements | | | | | |
| Neck BMD ($gcm^{-2}$) | 0.604 | 0.066 | 0.696 | 0.109 | 0.001 |
| Total BMC (g) | 1883 | 295 | 2138 | 274 | 0.003 |
| Total BMD ($gcm^{-2}$) | 0.92 | 0.12 | 0.87 | 0.10 | 0.111 |
| Troch BMD ($gcm^{-2}$) | 0.493 | 0.084 | 0.586 | 0.078 | <0.001 |
| Ward's BMD ($gcm^{-2}$) | 0.417 | 0.073 | 0.659 | 0.173 | <0.001 |
| Active Shape Model Modes | | | | | |
| Mode 2 | 7 | 19 | −5 | 16 | 0.019 |
| Mode 4 | −5 | 16 | 2 | 12 | 0.107 |
| Mode 5 | −4 | 12 | 2 | 12 | 0.094 |
| Mode 7 | 3.1 | 9.7 | −2.6 | 9.7 | 0.044 |
| Geometric Measurements | | | | | |
| H-Diam | 53.7 | 2.6 | 52.7 | 3.1 | 0.196 |
| N-Len | 110.2 | 5.3 | 109.7 | 7.6 | 0.759 |
| N-Wid | 38.2 | 3.2 | 37.8 | 2.8 | 0.671 |
| Ratios | | | | | |
| N-Wid/N-Len | 0.34 | 0.33 | 0.34 | 0.33 | 0.831 |
| | | 0.36 | | 0.36 | |
| H-Diam/N-Len | 0.49 | 0.0299 | 0.48 | 0.03 | 0.347 |

III) Discriminant Analysis

As all the modes of variation were distributed normally, stepwise linear discriminant analysis was used to select the best combination to build a classifier which could distinguish between the fracture and control groups. The discriminant analysis found that the $2^{nd}$, $4^{th}$, $5^{th}$ and $7^{th}$ modes of variation could be combined to build a classifier, Pshape, with 74% accuracy.

Discriminant analysis was carried out on variables Pshape, WARD'S BMD, TOTAL BMD, TOTAL BMC, NECK BMD and TROCH BMD using each as the sole discriminator. As can be seen from Table 4, the Pshape variable (accuracy 74%, area under ROC 0.81) was more accurate than most of the BMD measurements, with only WARD'S BMD (accuracy 82%, area under ROC 0.95) being a more powerful classifier, although this difference was not found to be significant by ROC analysis.

Table 4 shows the percentage accuracy of classification into fracture or control groups using linear discriminant analysis.

TABLE 4

| Variable | Accuracy (%) | Area under ROC |
|---|---|---|
| Ward's HMD | 82 | 95 |
| Pshape | 74 | 81 |
| Neck BMD | 74 | 79 |
| Total BMC | 70 | 74 |
| Troch BMD | 68 | 79 |
| Total BMD | 66 | 63 |
| Geometric ratio (H-Diam/N-Len) | 60 | 59 |
| Geometric (H-Diam) | 58 | 59 |
| Pshape and Ward's BMD | 90 | 96 |
| Pshape and Neck BMD | 82 | 89 |

Stepwise discriminant analysis was also used to build classifiers from the geometrical measurements and ratios. None of the geometrical variables were strong enough to be selected by the stepwise analysis. Linear discriminant analysis was performed on each of these variables independently with the following results: N-Wid (54%), H-Diam (58%), N-Len (56%), N-Wid/N-Len (50%), H-Diam/N-Len (60%). These results show that the geometrical variables were weaker discriminators than either BMD or ASM measurements.

Discriminant analysis was also used to test the ability of different combinations of variables to classify the two groups correctly. By combining the two best individual discriminators, WARDS BMD and Pshape, accuracy was increased to 90% (area under ROC 0.96). Discriminant analysis was also performed using the variables Pshape and NECK BMD to build a classifier. Both Pshape and NECK BMD achieved the same accuracy (74%) when used alone (area under ROC 0.81 and 0.79 respectively), whilst the combination of the two variables produced a classifier that was again substantially better than either measurement alone (accuracy 82%, area under ROC 0.89). Comparison of the area under the ROC showed that the improvement gained by adding the Pshape data to Neck BMD was statistically significant (P<0.05).

Logistic regression analysis showed that Pshape was still an independent predictor of hip factor after adjustment for age, body mass index and WARDS BMD (odds ratio 1.83, 95% CI 1.08-3.113) and also after adjustment for age, body mass index and NECK BMD (odds ratio 1.75, 95% CI 1.21-2.53). The odds ratios were calculated to represent the increase in the odds linked to a 10% increase in the estimated probability of belonging to the fracture group as calculated from the ASM data.

The use of ASM thus shows that a trained model can be used successfully to discriminate between a fracture and control group. The ASM alone performs better than most of the BMD measurements and all of the geometrical measurements. The best classifier tested combined the ASM data, Pshape, with WARD'S BMD to create a classifier with 90% accuracy. This was better than WARD'S BMD alone which, in turn, was better than the ASM data alone. All direct geometrical measures were inferior. Sensitivity analysis showed that only one of the fracture cases was missed. Analysis of Pshape with both Ward's triangle and femoral neck BMD showed that Pshape was independently associated with membership of the fracture group.

The independent modes of variation found by ASM are orthogonal and, therefore, each represents a change in the shape that happens independently of other changes. If a mode of variation is significantly different between the two groups, it will describe changes in shape affecting the whole of the proximal femur that potentially influence the likelihood of fracture. Analysis of these modes allows investigation of interactions, which are not made available by measuring changes in the individual geometrical properties of the femur.

Any 2D projection of a 3D structure, such as a DXA or X-ray image of the hip, is sensitive to the effects of rotation, foreshortening and magnification. Errors in geometrical measurements due to the position and rotation of the femur, positioning of the patient in the DXA or X-ray beam or the thickness of the patient's soft tissue are common and hard to adjust for after the scan. However, ASM is more robust than previous methods: the use of proportional, rather than absolute values will help to reduce the errors caused by magnification and with a sufficiently large training set, analysis of the modes of variation may be used to identify and correct for rotational artefacts.

EXAMPLE 2

A) Materials and Methods

I) Image Acquisition

The same set of images was analysed as in Example 1.

II) Region Selection

Figure 3:
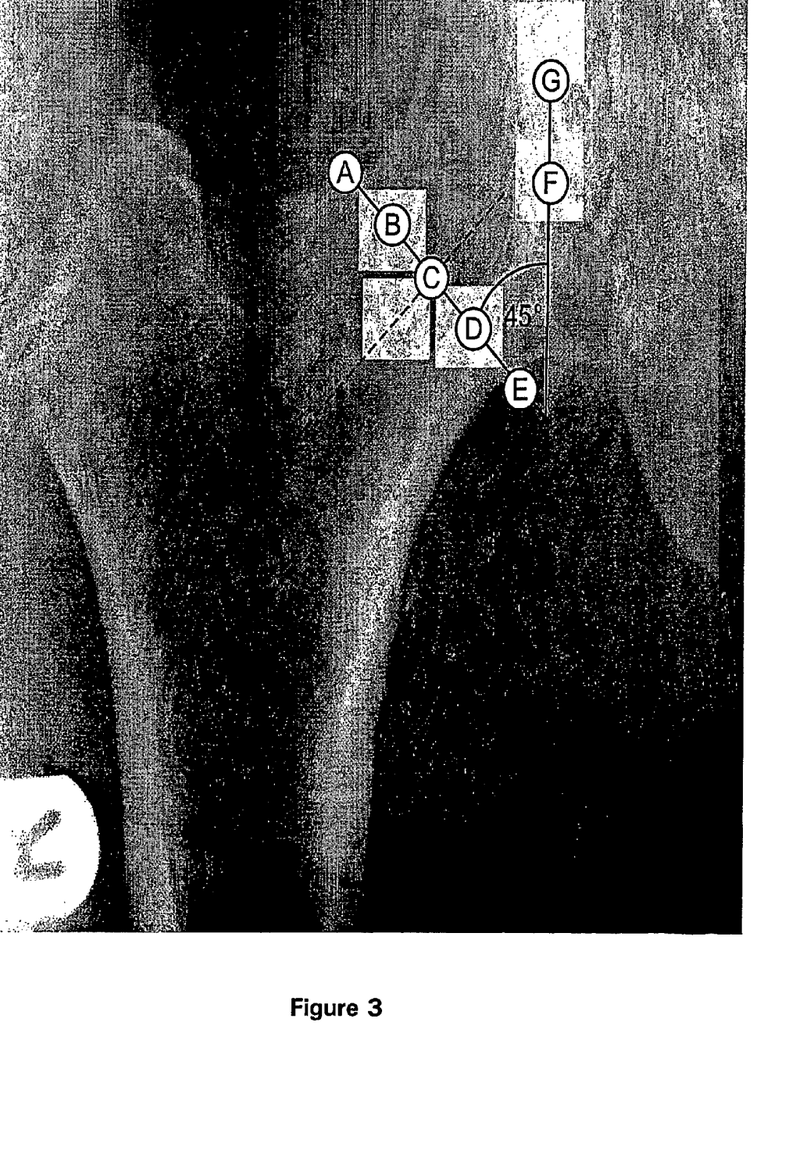
FIG. 3 shows a typical radiograph of the proximal femur showing how regions of interest (ROIs) for texture analysis can be located by points A to G, determined by the femoral head and neck, Points A and E marking the femoral neck width, Points B, C and D lying at 25%, 50% and 75% along this line, Point F being the centre point of the femoral head, and Point G being half the diameter of the femoral head at an angle of 45 degrees to the neck width, 135 degrees to the neck shaft, shown as a grey dashed line.

To ensure reproducibility, the location of five regions of interest (ROIs) was determined in relation to the centre and angle of the narrowest part of the femoral neck and the centre and diameter of the femoral head, as shown in FIG. 3. The femoral head was described by a best-fit circle, calculated from a series of manually marked points around the outline of the femoral head. Between 15 and 20 evenly spaced points were used to describe the outline, depending on the size of the head. The diameter and centre (marked as F in FIG. 3) of the femoral head were then taken from this circle.

The narrowest part of the neck (neck-width) was determined using two automatic edge traces, marking the upper and lower outlines of the femoral neck. The first point and the direction for each trace were marked manually; the edge of the neck could then be identified automatically. The neck width (A-E) was calculated by finding the smallest Euclidean distance between the traces. The centre of the neck was located at the mid-point of this line (point C) and the axis of the femoral neck was taken to be a line perpendicular to this through the centre of the neck (dashed line).

Each ROI was 256×256 pixels and was selected from either the upper region of the head (UH), the central region of the head (CH), the upper region of the neck (UN), the Ward's triangle (WA) or the lower region of the neck (LN). The points and regions were identified using a macro written for Image Pro Plus software (version 4.1.0.0, Media Cybernetics, Silver Spring, Md.). The top right corner of the WA region was located at the midpoint of the neck width (point C). Points B and D were placed 25% and 75% of the way along the neck width and used as the midpoints of the UN and LN regions respectively. Point F, the centre of the femoral head marked the centre of the CH region and point G, the centre of the base of the UH region. Point G was placed one half of the femoral head diameter above point F, at a 45-degree angle to the neck width (A-E).

III) Region Analysis

Analysis was performed using Matlab software (version 6.1.0, MathWorks Inc, Natick, Mass.). A fast Fourier transform was generated for each ROI and three profiles were generated using data from the power spectrum. Firstly a global or circular profile (CircP) was generated, composed of the magnitude at each frequency averaged across all angles.

The angle of preferred orientation was calculated by finding the angle of the maximum in the power spectrum for the first 25 frequencies. The median of the values plus 90° was taken as the angle of preferred orientation for each image. As the Fourier power spectrum is symmetrical, angles were calculated between 0° and 180°. Two more profiles were then generated, parallel with (ParP) and perpendicular to (PerP) the angle of preferred orientation. In this case the average value was calculated at each frequency from all points lying within ±5° of the desired angle.

IV) Principal Component Analysis

Principal Component Analysis was used to model statistically the shape of each set of profiles (parallel, perpendicular and circular). After performing each PCA, a scree plot was generated by plotting the eigenvalues (representing the proportion of variance described by each component) against the component number. The eigenvalues are associated with the components in decreasing order, with the largest eigenvalue associated with the first component and the smallest with the last. In each case, the first N principal components were selected for analysis using the scree test to find an 'elbow' in the slope of the plot. This is used as a threshold between the components that contain useful information and those that can be attributed to noise. These components were then used as input variables for further analysis.

V) Fractal Analysis

Fractal analysis was performed on each profile using a method similar to the Fourier transform technique described by Majumdar et al (Medical Physics 1999; 26(7); 1330-1340). The average power spectrum of the circular profile was plotted on a log-log scale, three approximately linear regions were defined and the gradient (slope) of a straight line fitted to each region was found; slope A, a 'coarse' slope, where the log of the frequency is less than or equal to 1.0; slope B, a 'medium' slope, where the log of the frequency lies between 1.0 and 1.75; and slope C, a 'fine' slope, where the log of the frequency is above 1.75. The fractal dimension was calculated using the formula suggested by Majumdar et al:

$$D_{FFT} = (7 - \text{slope})/2.$$

VI) Statistical Analysis

Stepwise discriminant analysis was used to select principal components that could be combined to build a linear classifier. If the stepwise procedure failed to select any components, the most accurate of the individual components was chosen. The same procedure was used to discriminate between the groups using the fractal dimension. Measurement of the area under the ROC curve was used to compare the classifiers built using the discriminant analysis.

A three way ANOVA was applied in order to determine whether there were significant differences between the performance of classifiers depending on the type of analysis, the profile used or the region analysed. Pearson product moment correlation was applied to examine the relationship with age, BMI and Neck BMD for the strongest classifiers. T-tests, correlation and ANOVA were performed using SigmaStat (version 2.03, SPSS Science, Chicago). Principal Component Analysis, discriminant analysis, and measurement of the area under the ROC curve were calculated using SPSS (version 10 SPSS Science, Chicago).

B) Results

There were no significant differences between the age, height, weight or BMI of the fracture and control groups.

Table 5 shows the area under the ROC curve (Az) for PCA analysis by region of the femoral neck for the circular, perpendicular and parallel profiles respectively.

TABLE 5

| Region | Circular (95% CI) | Parallel (95% CI) | Perpendicular (95% CI) |
|---|---|---|---|
| Upper head | 0.76 (0.63-0.89) | 0.57 (0.41-0.73) | 0.84 (0.73-0.95) |
| Central head | 0.59 (0.43-0.75) | 0.56 (0.40-0.73) | 0.84 (0.72-0.95) |
| Upper neck | 0.72 (0.58-0.86) | 0.72 (0.57-0.86) | 0.67 (0.52-0.82) |
| Ward's triangle | 0.74 (0.61-0.88) | 0.61 (0.45-0.76) | 0.71 (0.56-0.86) |
| Lower neck | 0.71 (0.56-0.85) | 0.55 (0.39-0.71) | 0.93 (0.87-1.00) |

An overall mean value of 0.70 was observed (standard deviation 0.11), with the best results coming from the circular and perpendicular profiles. The 5 largest areas under the ROC curve were obtained by PCA of the perpendicular profile of the lower neck, upper and central head regions (see Table 6 below) (Az=0.93, 0.84 and 0.84 respectively), followed by PCA analysis of the circular profile in the upper head region (Az=0.76) and, finally, fractal analysis of the parallel profile in the upper neck region (Az=0.75).

A three-way analysis of variance was used to examine differences in performance due to the region, profile or type of analysis used. It showed that overall PCA analysis performed significantly better than fractal analysis (P<0.05) and that analysis of both the perpendicular and circular profiles performed significantly better than the parallel profile (P<0.05). No significant differences were found between the different regions of the femoral neck (P=0.241).

TABLE 6

| Analysis | Profile | ROI | Az (95% CI) | $R_{BMD}$ (p) | $R_{age}$ (p) | $R_{BMI}$ (p) |
|---|---|---|---|---|---|---|
| PCA | PerP | LN | 0.93 (0.87-1.00) | 0.09 (0.55) | 0.14 (0.34) | -0.08 (0.58) |
| PCA | PerP | UH | 0.84 (0.73-0.95) | 0.09 (0.52) | -0.17 (0.24) | -0.03 (0.86) |
| PCA | PerP | CH | 0.84 (0.72-0.95) | 0.06 (0.70) | 0.27 (0.055) | -0.11 (0.46) |
| PCA | CircP | UH | 0.76 (0.63-0.89) | -0.16 (0.28) | -0.15 (0.29) | 0.07 (0.62) |
| Fractal | ParP | UN | 0.75 (0.61-0.89) | -0.30 (0.034) | 0.25 (0.081) | -0.04 (0.78) |

Table 6 shows the area under the ROC curve (Az) for each of the best 5 classifiers, and the correlation with age $R_{age}$, femoral neck BMD ($R_{BMD}$) and body mass index ($R_{BMI}$), and associated significance values (P).

Thus, texture analysis of standard radiographs using a fast Fourier transform can yield variables that are significantly associated with fracture after adjustment for age, body mass index and Neck-BMD. Both PCA and fractal analysis, both derived from the FFT data, could be used to discriminate successfully between the groups, PCA being stronger than fractal dimension. The best results from this study were uncorrelated with Neck-BMD, age or BMI.

PCA considerably reduces the number of variables required to characterise an image via its power spectrum. For example, in Example 2, a 256×256 pixel ROI (65,536 pixels) is selected, the Fourier transform is generated, and a profile of 128 spatial frequency values is generated. PCA is then performed, and in each case was able to describe over 70% of the variance present in the data using only 5 components or fewer. Overall, the performance of principal components analysis was significantly stronger than that of fractal analysis (P<0.01). An advantage of PCA is the ability to summarise the information present in the dataset with a small number of components via an economical mapping of the variance present in the data. In addition, the property of orthogonality between these components ensures that the variables generated are linearly independent. Benefits can also be found by the use of a model built on the mathematical distributions present in the data, rather than expecting the data to meet a given mathematical property, such as fitting a fractal or normal distribution.

EXAMPLE 3

A) Materials and Methods

Data from the radiographic study of trabecular structure described in Example 2 was reanalysed using the first 14 Fourier components, in order to simulate the lower resolution of a DXA scan. The method employed in Example 2 was used.

B) Results

74% of subjects were correctly identified from the lower resolution images (Az=0.71, 95% CI=0.56-0.86). This is a similar degree of accuracy as the BMD value (74% accuracy, Az=0.79, 95% CI 0.66-0.91), and the ASM analysis (74% accuracy, Az=0.81, 95% CI=0.69-0.93).

When the low resolution result was combined with ASM and BMD data, even more accurate results were obtained, resulting in the ability to discriminate between fracture and control groups with 84% accuracy (Az=0.913, 95% CI=0.837-0.990). The low resolution Fourier Transform was not significantly correlated to either the shape, measured by the ASM classifier (r=−0.716, P=0.220) or BMD (r=0.159, P=0.269).

These results thus show that measurements obtained from the shape and trabecular structure of the femur can be applied to DXA images, thus making it possible for these results to be combined with BMD data to improve fracture risk prediction.

The invention claimed is:

1. Apparatus for predicting bone fracture risk in a osteoporotic patient, comprising:
   a Dual X-ray Absorptiometry scanner configured to scan a body area of the patient to thereby produce a Dual X-ray Absorptiometry image of the body part within said body area;
   an image analysis module configured to perform shape analysis using an Active Shape Model and to perform texture analysis of the Dual X-ray Absorptiometry image to thereby generate an image data set representative of aspect of the shape of body part and the structure of bone within the body area; and
   a data comparison module having a database of comparative data sets from Dual X-ray Absorptiometry images of control subjects, to compare the Active Shape Model data set generated from Dual X-ray Absorptiometry image of the patient with the comparative data sets in the database by examining how the location of landmark points deviates from a mean co-ordinates of the comparative data sets, to thereby predict the risk of bone fracture in the patient.

2. The apparatus according to claim 1, wherein the body part is a proximal femur.

3. The apparatus according to claim 1 configured to analyze different body parts.

4. The apparatus according to claim 1 configured to analyze more than one of proximal femur, wrist, ankle, hand, and spine.

5. Apparatus according to claim 1, wherein the image analysis module is configured to analyze aspects of the Dual X-ray Absorptiometry image using Fourier transforms and Principal Component Analysis, for generating a texture data set representative of the texture of the body part.

6. Apparatus according to claim 5, wherein the Dual X-ray Absorptiometry image is digitised and regions of interest identified in the image, from which a power spectrum is obtained from a Fourier transform of each region of interest, and profiles of each region produced, the Principal Component Analysis generating a data set from each profile, which is to be compared with the database of comparative data sets.

7. Apparatus according to claim 1 is configured to compare i) a value obtained from comparison of the image data set for the Dual X-ray Absorptiometry image of the patient or subject with the database of comparative data sets, with ii) bone mineral density data obtained from the Dual X-ray Absorptiometry image.

8. An apparatus for measuring the progression of a disorder which affects the shape and/or trabecular structure of bone in a patient, the apparatus comprising:
   a Dual X-ray Absorptiometry scanner for scanning a body area of the patient to thereby produce a Dual X-ray Absorptiometry image of a body part within said body area;
   an image analysis module configured to perform shape analysis using an Active Shape Model and to perform texture analysis of the Dual X-ray Absorptiometry image to thereby generate an image data set representative of aspects of the shape of the body part and the structure of bone within the body area; and
   a data comparison module comprising a database of comparative data sets from Dual X-ray Absorptiometry images of control subjects, to compare the Active Shape Model data set generated from the Dual X-ray Absorptiometry image of the patient with the comparative data sets in the database by examining how the location of landmark points deviates from a mean co-ordinates of the comparative data sets, to thereby provide a measure of the progression of the disorder in the patient.

9. The apparatus according to claim 8, wherein the disorder is osteoarthritis.

10. The apparatus according to claim 8, wherein the disorder is Paget's disease.

11. The apparatus according to claim 8, wherein the body part is a proximal femur.

12. The apparatus according to claim 8 configured to analyze different body parts.

13. The apparatus according to claim 8 for analysing more than one of the proximal femur, wrist, ankle, hand and spine.

14. The Apparatus according to claim 8, wherein the image analysis module is configured to analyze aspects of the Dual X-ray Absorptiometry image using Fourier transforms and Principal Component Analysis, for generating a texture data set representative of the texture of the body part.

15. The apparatus according to claim 14, wherein the Dual X-ray Absorptiometry image is digitized and regions of interest identified in the image, from which a power spectrum is obtained from a Fourier transform of each region of interest, and profiles of each region produced, the Principal Component Analysis generating a texture data set from each profile, which is to be compared with the database of comparative data sets.

16. The apparatus according to claim 8 configured to compare i) a value obtained from comparison of the image data set for the Dual X-ray Absorptiometry image of the patient or subject with the database of comparative data sets, with ii) bone mineral density data obtained from the Dual X-ray Absorptiometry image.

17. An apparatus for predicting a risk of osteoarthritis in a patient, the apparatus comprising:
a Dual X-ray Absorptiometry scanner for scanning a body area of the patient to thereby produce a Dual X-ray Absorptiometry image of a body part within said body area;
an image analysis module configured to perform shape analysis using an Active Shape Model and to perform texture analysis of the Dual X-ray Absorptiometry image to thereby generate an image data set representative of aspects of the shape of the body part and the structure of bone within the body area; and
a data comparison module comprising a database of comparative data sets from Dual X-ray Absorptiometry images of control subjects, to compare the Active Shape Model data set generated from the Dual X-ray Absorptiometry image of the patient with the comparative data sets in the database by examining how the location of landmark points deviates from a mean co-ordinates of the comparative data sets, to thereby predict the risk of osteoarthritis in the patient.

18. The apparatus according to claim 17, wherein the body part is a proximal femur.

19. The apparatus according to claim 17 configured to analyze different body parts.

20. The apparatus according to claim 17 configured to analyze more than one of the proximal femur, wrist, ankle, hand and spine.

21. The apparatus according to claim 17, wherein the image analysis module is configured to analyze aspects of the Dual X-ray Absorptiometry image using Fourier transforms and Principal Component Analysis, for generating a texture data set representative of the texture of the body part.

22. The apparatus according to claim 21, wherein the Dual X-ray Absorptiometry image is digitized and regions of interest identified in the image, from which a power spectrum is obtained from a Fourier transform of each region of interest, and profiles of each region produced, the Principal Component Analysis generating a texture data set from each profile, which is to be compared with the database of comparative data sets.

23. The apparatus according to claim 17 configured to compare i) a value obtained from comparison of the image data set for the Dual X-ray Absorptiometry image of the patient or subject with the database of comparative data sets, with ii) bone mineral density data obtained from the Dual X-ray Absorptiometry image.

24. The apparatus for measuring non-pathological changes in a subject associated with age, gender, body mass index and/or genetics, the apparatus comprising:
a Dual X-ray Absorptiometry scanner for scanning a body area of the subject to thereby produce a Dual X-ray Absorptiometry image of a body part within said body area;
an image analysis module configured to perform analysis using an Active Shape Model shape and to perform texture analysis of the Dual X-ray Absorptiometry image to thereby generate an image data set representative of aspects of the shape of the body and the structure of bone within the body area; and
a data comparison module comprising a database comparative data sets from Dual X-ray Absorptiometry images of control subjects, to compare the Active Shape Model data set generated from the Dual X-ray Absorptiometry image of the patient with the comparative data sets in the database by examining how the location of landmark points deviates from a mean co-ordinates of the comparative data sets, to thereby provide a measure of said non-pathological changes.

25. The apparatus according to claim 24, wherein the body part is a proximal femur.

26. The apparatus according to claim 24 configured to analyze different body parts.

27. The apparatus according to claim 24 configure to analyze more than one of the proximal femur, wrist, ankle, hand and spine.

28. The apparatus according to claim 24, wherein the image analysis module is configured to analyze aspects of the Dual X-ray Absorptiometry image using Fourier transforms and Principal Component Analysis, for generating a texture data set representative of the texture of the body part.

29. The apparatus according to claim 28, wherein the Dual X-ray Absorptiometry image is digitized and regions of interest identified in the image, from which a power spectrum is obtained from a Fourier transform of each region of interest, and profiles of each region produced, the Principal Component Analysis generating a texture data set from each profile, which is to be compared with the database of comparative data sets.

30. The apparatus according to claim 24 configured to compare i) a value obtained from comparison of the image data set for the Dual X-ray Absorptiometry image of the patient of subject with the database of comparative data sets, with ii) bone mineral density data obtained from the Dual X-ray Absorptiometry image.

31. The apparatus for quantifying deformation of a proximal femur of a patient, the apparatus comprising:
a Dual X-ray Absorptiometry scanner for scanning a body area of the patient to thereby produce a Dual X-ray Absorptiometry image of a body part within said body area;
an image analysis module configured to perform shape analysis using an Active Shape Model and to perform texture analysis of the Dual X-ray Absorptiometry image to thereby generate an image data set representative of aspects of the shape of the body part and the structure of bone within the body area; and a data comparison module comprising a database of comparative data sets from Dual X-ray Absorptiometry images of control subjects, to compare the Active Shape Model data set generated from the Dual X-ray Absorptiometry image of the patient with the comparative data sets in the database by examining how the location of landmark points deviates from a mean co-ordinates of the comparative data sets, to thereby quantify deformation of the proximal femur.

32. The apparatus according to claim 31, wherein the image analysis module is configured to analyze aspects of the Dual X-ray Absorptiometry image using Fourier transforms and Principal Component Analysis, for generating a texture data set representative of the texture of the body part.

33. The apparatus according to claim 32, wherein the Dual X-ray Absorptiometry image is digitized and regions of interest identified in the image, from which a power spectrum is obtained from a Fourier transform of each region of interest, and profiles of each region produced, the Principal Component Analysis generating a texture data set from each profile, which is to be compared with the database of comparative data sets.

34. The apparatus according to claim 31 configured to compare i) a value obtained from comparison of the image data set for the Dual X-ray Absorptiometry image of the patient or subject with the database of comparative data sets, with ii) bone mineral density data obtained from the Dual X-ray Absorptiometry image.

* * * * *